United States Patent [19]

Farha, Jr. et al.

[11] 4,371,728
[45] Feb. 1, 1983

[54] SELECTIVE REMOVAL OF OLEFINS OVER ZINC TITANATE PROMOTED WITH SELECTED METALS

[75] Inventors: Floyd E. Farha, Jr.; Lloyd E. Gardner, both of Bartlesville, Okla.

[73] Assignee: Phillips Petroleum Company, Bartlesville, Okla.

[21] Appl. No.: 326,776

[22] Filed: Dec. 2, 1981

Related U.S. Application Data

[60] Division of Ser. No. 190,004, Sep. 23, 1980, Pat. No. 4,313,820, which is a continuation-in-part of Ser. No. 125,438, Feb. 28, 1980, abandoned.

[51] Int. Cl.³ .............................................. C07C 7/163
[52] U.S. Cl. .................................. 585/258; 208/143; 252/411 S; 252/475; 585/259
[58] Field of Search ............... 208/143; 585/258, 259; 252/475, 411 S

[56] References Cited

U.S. PATENT DOCUMENTS

| 2,037,790 | 4/1936 | Ipatieff | 423/230 |
|---|---|---|---|
| 2,279,198 | 4/1942 | Huppke | 208/134 |
| 2,298,347 | 10/1942 | Corson | 208/215 |
| 2,393,288 | 1/1946 | Byrns | 208/46 |
| 2,591,525 | 4/1952 | Engel | 208/214 |
| 3,105,811 | 11/1963 | Engel | 208/60 |
| 3,427,253 | 2/1969 | Boost | 423/230 |
| 4,029,599 | 6/1977 | Pegels | 208/216 R |
| 4,052,296 | 10/1977 | Montagna | 208/216 R |
| 4,071,439 | 1/1978 | Yanik | 208/216 R |
| 4,128,205 | 12/1978 | Mikovsky | 208/216 R |
| 4,144,277 | 3/1979 | Walker | 260/666 A |
| 4,155,835 | 5/1979 | Antol | 208/89 |
| 4,218,346 | 8/1980 | Walker et al. | 252/475 |
| 4,228,040 | 10/1980 | Bertus et al. | 252/475 |
| 4,313,820 | 2/1982 | Farha, Jr. et al. | 208/213 |

Primary Examiner—Delbert E. Gantz
Assistant Examiner—A. Pal

[57] ABSTRACT

Hydrogen sulfide is removed from a fluid stream by contacting the fluid stream which contains hydrogen sulfide with an absorbing composition comprising zinc, titanium and at least one promoter selected from the group consisting of vanadium, chromium, manganese, iron, cobalt, nickel, molybdenum, rhenium, and compounds thereof. If organic sulfur compounds are present in the fluid stream, the absorbing composition acts as a hydrodesulfurization catalyst to convert the sulfur in the organic sulfur compounds to hydrogen sulfide which is subsequently removed from the fluid stream by the absorbing composition. If olefin contaminants are present in the fluid stream, the absorbing composition acts as hydrogenation catalyst to hydrogenate the olefin contaminants to paraffins.

15 Claims, No Drawings

SELECTIVE REMOVAL OF OLEFINS OVER ZINC TITANATE PROMOTED WITH SELECTED METALS

This application is a division of application Ser. No. 190,004, filed Sept. 23, 1980 now U.S. Pat. No. 4,313,820, issued Feb. 2, 1982 which is a continuation-in-part of application Ser. No. 125,438, filed Feb. 28, 1980, now abandoned.

This invention relates to an improved process for removing sulfur from fluid streams and/or hydrogenating olefins contained in the fluid streams. In one aspect this invention relates to an improved process for selectively removing hydrogen sulfide from fluid streams. In another aspect this invention relates to an improved process for hydrodesulfurizing (HDS) organic sulfur compounds contained in a fluid stream to convert the sulfur in the organic sulfur compounds to hydrogen sulfide and for removing the thus produced hydrogen sulfide, and any other hydrogen sulfide present in the fluid stream, from the fluid stream. In still another aspect this invention relates to a process for hydrogenating olefins to paraffins to improve the odor of a fluid containing the olefins.

Removal of sulfur from fluid streams can be desirable or necessary for a variety of reasons. If the fluid stream is to be burned as a fuel, removal of sulfur from the fluid stream can be necessary to prevent environmental pollution. If the fluid stream is to be processed, removal of the sulfur is often necessary to prevent poisoning of sulfur-sensitive catalysts or to satisfy other process requirements.

A variety of methods are available to remove sulfur from a fluid stream if the sulfur is present as hydrogen sulfide. These methods include using alkaline reagents that unselectively absorb all acid gases. Other methods include the use of selective solid adsorbents such as zinc oxide and bog iron ore. However, in general these solid adsorbents are not regenerable to their original form and must be discarded when they have become completely sulfided.

It is thus an object of this invention to provide an improved process for selectively removing hydrogen sulfide from fluid streams. It is a further object of this invention to provide an improved removal or absorbing composition which possesses the property of being regenerable to the original absorbing composition state in the presence of oxygen.

If the sulfur is present in the fluid stream in the form of an organic sulfur compound, the organic sulfur compound may be hydrodesulfurized to convert the sulfur in the organic sulfur compound to hydrogen sulfide which can be removed from the fluid stream by an absorbing composition.

It is thus another object of this invention to provide a process for not only removing hydrogen sulfide from a fluid stream but also hydrodesulfurizing organic sulfur compounds to convert the sulfur in the organic sulfur compounds to hydrogen sulfide which can then be selectively removed from the fluid stream.

The presence of olefin contaminants in a fluid may result in a foul odor associated with the fluid. Also, the olefin contaminants may be oxidized to even more malodorous products when released into the air. This is particularly the case in aerosol propellants. It is thus another object of this invention to provide a process for hydrogenating olefin contaminants in a fluid and particularly in aerosol propellants.

In accordance with the present invention, an absorbing composition comprising zinc, titanium and a promoter is utilized to selectively remove hydrogen sulfide, if present, from a fluid stream. The promoter is at least one member selected from the group consisting of vanadium, chromium, manganese, iron, cobalt, nickel, molybdenum, rhenium and compounds thereof. The absorbing composition can be formed by combining zinc oxide and titanium dioxide by any of the methods known in the art to form zinc titanate. The promoter can then be added to the zinc titanate. Once the absorbing composition has been prepared, fluid streams are contacted with the absorbing composition under suitable absorbing conditions to substantially reduce the concentration of hydrogen sulfide in the fluid stream.

The absorbing composition also acts as a hydrodesulfurization catalyst if organic sulfur compounds are present in the fluid stream. Under suitable hydrodesulfurization conditions the organic sulfur compounds are converted to hydrogen sulfide in the presence of the absorbing composition which acts as a hydrodesulfurization catalyst. After conversion to hydrogen sulfide, the sulfur will be removed from the fluid stream by the absorbing composition.

The absorbing composition also acts as an olefin hydrogenation catalyst if olefin contaminants are present in the fluid stream. Under suitable olefin hydrogenation conditions the olefin contaminants are hydrogenated to paraffins in the presence of the absorbing composition which acts as an olefin hydrogenation catalyst. The paraffins do not have the undesirable odor and are not readily oxidized to malodorous products when released into the air.

It is believed that the hydrogen sulfide is being absorbed by the absorbing composition and thus the terms "absorption process" and "absorbing composition" are utilized for the sake of convenience. However, the exact chemical phenomenon occurring is not the inventive feature of the process of the present invention and the use of the term "absorb" in any form is not intended to limit the present invention.

Hereinafter, the process of the present invention is referred to by a plurality of terms depending on the reactions occurring. Terms utilized include selective absorption or absorption process, hydrodesulfurization process, olefin hydrogenation process and combinations thereof. The term "absorbing composition" is utilized to refer to the promoted zinc titanate in general although the term "catalyst/absorbing composition" is also utilized in some cases where the promoted zinc titanate is acting as a hydrodesulfurization catalyst, as a hydrogenation catalyst and/or as an absorbing composition.

The selective absorption process is preferably carried out in cycles comprising an absorption period and a regeneration period for the absorbing composition. The absorption period comprises contacting a fluid stream containing hydrogen sulfide with the absorbing composition to thereby selectively remove hydrogen sulfide from the fluid stream. The absorbing composition becomes sulfided during the absorption period. When the absorbing composition becomes sulfided to the point that regeneration is desirable, preferably when it is substantially completely sulfided, a gas containing molecular oxygen is passed in contact with the absorbing composition to regenerate the absorbing composition and convert the absorbed sulfur to an oxide.

The hydrodesulfurization/absorption process is also preferably carried out in cycles comprising a reaction period and a regeneration period for the catalyst. The reaction period comprises contacting a fluid stream containing organic sulfur compounds with the hydrodesulfurization/absorption composition to thereby convert the sulfur in organic sulfur compounds in the fluid stream to hydrogen sulfide. The hydrodesulfurization/absorption composition becomes sulfided during the reaction period. When the composition becomes substantially completely sulfided, a gas containing molecular oxygen is passed in contact with the hydrodesulfurization/absorption composition to regenerate the composition and to convert the absorbed sulfur to an oxide.

Olefin hydrogenation may be combined with either a selective absorption process or a hydrodesulfurization/absorption process. Olefin hydrogenation may also occur when sulfur is not present in the fluid stream being contacted with the promoted zinc titanate. In all of these cases the process is still carried out in cycles comprising a reaction period and a regeneration period. It is, however, noted that, if sulfur is not present in the fluid stream, the length of the reaction period is determined by coke buildup on the catalyst.

If desired, at least one oxidation promoter selected from the group consisting of ruthenium, rhodium, palladium, silver, tungsten, iridium, platinum, and compounds thereof may also be present to promote the regeneration of the absorbing composition.

The chemical changes that are believed to occur in the absorbing composition during this cyclic process where sulfur is present are summarized in the following equations:

(I) $Zn_2TiO_4 + 2H_2S \rightarrow 2ZnS + TiO_2 + 2H_2O$ (II) $ZnS + Oxygen \rightarrow ZnO + SO_x$ (III) $2ZnO + TiO_2 \rightarrow Zn_2TiO_4$ Other objects and advantages of the invention will be apparent from the foregoing description of the invention and the appended claims as well as from the detailed description of the invention which follows.

Any suitable organic sulfur compound may be hydrodesulfurized in accordance with the present invention. Suitable organic sulfur compounds include sulfides, disulfides, mercaptans, carbonyl sulfides, thiophenes, benzothiophenes, dibenzothiophenes and mixtures of any two or more thereof.

The absorbing composition of the present invention may be utilized to remove hydrogen sulfide from any suitable fluid stream. The hydrogen sulfide may be produced by the hydrodesulfurization of organic sulfur compounds or may be originally present in the fluid stream as hydrogen sulfide. Suitable fluid streams include light hydrocarbons such as methane, ethane and natural gas, petroleum products and products from extraction and/or liquefaction of coal and lignite, products from tar sands, products from shale oil, coal derived synthesis gas, gases such as hydrogen and nitrogen, gaseous oxides of carbon, steam, and the inert gases such as helium and argon. Gases that adversely affect the removal of hydrogen sulfide and which should be absent from the fluid streams being processed are oxidizing agents such as molecular oxygen, the halogens, the oxides of nitrogen, and the like.

The absorbing composition of the present invention may be utilized to remove hydrogen sulfide from olefins such as ethylene. However, this process should be carried out in the absence of free hydrogen to avoid hydrogenation. Olefin streams should not be hydrodesulfurized as this may result in undesirable hydrogenation of at least a portion of the olefins to paraffins.

The absorbing composition of the present invention may be utilized to hydrogenate olefin contaminants in any suitable fluid stream. It is particularly desirable to remove olefin contaminants from $C_3$ and $C_4$ paraffins such as isobutane, n-butane and propane which are utilized as aerosol propellants. The present invention is particularly directed to hydrogenating light olefins such as ethylene, propylene, n-butenes, isobutene, n-pentenes and branched pentenes contained in aerosol propellants.

The absorbing composition employed in the process of the present invention is a composition consisting essentially of zinc, titanium and a promoter. The promoter is at least one member selected from the group consisting of vanadium, chromium, manganese, iron, cobalt, nickel, molybdenum, rhenium, and compounds thereof. At least one oxidation promoter selected from the group consisting of ruthenium, rhodium, palladium, silver, tungsten, iridium, platinum, and compounds thereof, may also be present in the absorbing composition. The zinc and titanium are generally present in the absorbing composition as zinc titanate. The promoters may be present in the absorbing composition as oxides, sulfides or as the free element. A preferred combination of promoters is cobalt oxide plus molybdenum oxide where the cobalt:molybdenum atomic ratio is in the range of 0.3:1 to about 0.8:1.

The zinc titanate base of the absorbing composition may be prepared by intimately mixing suitable portions of zinc oxide and titanium dioxide, preferably in a liquid such as water, and calcining the mixture in a gas containing molecular oxygen at a temperature in the range of about 650° C. to about 1050° C., preferably in the range of about 675° C. to about 975° C. A calcining temperature in the range of about 800° C. to about 850° C. is most preferred because the surface area of the catalyst is maximized in this temperature range thus producing a more active catalyst. The titanium dioxide used in preparing the zinc titanate preferably has extremely fine particle size to promote intimate mixing of the zinc oxide and titanium dioxide. This produces a rapid reaction of the zinc oxide and titanium dioxide which results in a more active catalyst. Preferably the titanium dioxide has an average particle size of less than 100 millimicrons and more preferably less than 30 millimicrons. Flame hydrolyzed titanium dioxide has extremely small particle size and is particularly preferred in preparing the catalyst. The atomic ratio of zinc to titanium can be any suitable ratio. The atomic ratio of zinc to titanium will generally lie in the range of about 1:1 to about 3:1 and will preferably lie in the range of about 1.8:1 to about 2.2:1 because the activity of the absorbing composition is greatest for atomic ratios of zinc to titanium in this preferred range. The term "zinc titanate" is used regardless of the atomic ratio of zinc to titanium.

The zinc titanate base of the absorbing composition may also be prepared by coprecipitation from aqueous solutions of a zinc compound and a titanium compound. The aqueous solutions are mixed together and the hydroxides are precipitated by the addition of ammonium hydroxide. The precipitate is then washed, dried and calcined as described in the preceding paragraph. This method of preparation is less preferred than the mixing method because the zinc titanate prepared by the coprecipitation method is softer than the zinc titanate prepared by the mixing method.

The promoter, at least one member of which is selected from the group consisting of vanadium, chromium, manganese, iron, cobalt, nickel, molybdenum, rhenium, and compounds thereof, is generally present in the absorbing composition in the oxide form. The oxidation promoter, at least one member of which is selected from the group consisting of ruthenium, rhodium, palladium, silver, tungsten, iridium, platinum, and compounds thereof will generally be present in the absorbing composition as the free metal or the oxide form if utilized. The promoter or combination of promoters can be added to the zinc titanate by any method known in the art. The promoter or combination of promoters can be added to the zinc titanate as powdered oxide and dispersed by any method known in the art such as rolling, shaking or stirring. The preferred method of adding the promoter is by impregnating the preformed zinc titanate with a solution of a compound of the promoting element. After impregnation, the absorbing composition is preferably dried to remove solvent and is then heated in air at a temperature in the range of about 500° to about 650° C., preferably about 540° C., before being utilized for the absorption process or hydrodesulfurization/absorption process. If more than one promoter is to be used, the absorbing composition is preferably dried and calcined after each promoter addition.

The concentration of the promoter in the absorbing composition may be any suitable concentration. The concentration of vanadium, chromium, manganese, iron, cobalt, nickel, or molybdenum expressed as an element, if present, will generally be in the range of about 0.4 to 16 weight percent based on the weight of the promoted absorbing composition. A combination of these promoters may be utilized. However, the total concentration of the promoters, expressed as an element, should be in the range of about 1 to about 28 weight percent based on the weight of the promoted absorbing composition. The concentration of rhenium, expressed as an element, will generally be in the range of about 0.05 to about 2.5 weight percent based on the weight of the promoted absorbing composition. The rhenium may also be utilized in combination with the vanadium, chromium, manganese, iron, cobalt, nickel, and molybdenum but again the total concentration of the promoters, expressed as an element, should not exceed 28 weight percent based on the weight of the promoted absorbing composition. The concentration of ruthenium, rhodium, palladium, silver, iridium or platinum, expressed as an element, if present, will generally be in the range of about 0.05 to about 2.5 weight percent based on the weight of the promoted absorbing composition. The concentration of tungsten, expressed as an element, if present, will generally be in the range of about 0.4 to about 16 weight percent based on the weight of the promoted absorbing composition. The oxidation promoters, if utilized, are always utilized in combination with the promoters, at least one member of which is selected from the group consisting of vanadium, chromium, manganese, iron, cobalt, nickel, molybdenum, rhenium, and compounds thereof. Again, the total concentration of the promoters, including the oxidation promoters, should not exceed 28 weight percent based on the weight of the promoted absorbing composition.

Either the elemental form of the promoters or any suitable compound of the promoters may be used to form the absorbing composition. Suitable compounds of the promoting elements that can be applied to zinc titanate by solution impregnation include the nitrates, sulfates, acetates and the like of chromium, manganese, iron, cobalt, nickel, and silver; ammonium salts of vanadates, molybdates, tungstates, rhenates and perrhenates; and nitrates, chlorides, or hexachloro ammonium salts of ruthenium, rhodium, palladium; and dihydrogen hexachloroplatinate.

The processes of the present invention can be carried out by means of any apparatus whereby there is achieved an alternate contact of the absorbing composition with the fluid stream and thereafter of the absorbing composition with a fluid containing molecular oxygen utilized to regenerate the absorbing composition. The process is in no way limited to the use of a particular apparatus. The process of this invention can be carried out using a fixed absorbing composition bed, fluidized absorbing composition bed or moving absorbing composition bed. Presently preferred is a fixed absorbing composition bed.

In order to avoid any casual mixing of the fluid stream which contains organic sulfur compounds, olefin contaminants and/or hydrogen sulfide with the oxygen-containing fluid utilized in the regeneration step, provision is preferably made for terminating the flow of the fluid stream to the reactor and subsequently injecting an inert purging fluid such as nitrogen, carbon dioxide or steam. Any sitable purge time can be utilized but the purge should be continued until all hydrocarbon and/or hydrogen are removed. Any suitable flow rate of the purge fluid may be utilized. Presently preferred is a purge fluid flow rate in the range of about 800 GHSV to about 1200 GHSV.

Any suitable temperature for the processes of the present invention may be utilized. For both absorption and olefin hydrogenation the temperature will generally be in the range of about 149° C. to about 538° C. and will more preferably be in the range of about 204° C. to about 399° C. For hydrodesulfurization the temperature will generally be in the range of about 205° C. to about 538° C. and will more preferably be in the range of about 260° C. to about 427° C.

Any suitable temperature may be utilized to regenerate the absorbing composition from its sulfided form back to the original absorbing composition form or to simply burn off carbon if only olefin hydrogenation is occurring. The temperature will generally be in the range of about 370° C. to about 815° C. A temperature of at least 540° C. is preferred to effect the conversion within a reasonable time.

Any suitable pressure for the processes of the present invention can be utilized. For hydrodesulfurization the pressure will range of from about atmospheric to about 1,000 psig. This pressure is the sum of the partial pressure of the fluid stream plus the partial pressure of the added hydrogen. Preferably, the pressure will be in the range of from about 15 psig to about 200 psig with about 80 psig being particularly preferred for economy of operation as a cyclic process. The low pressure at which the hydrodesulfurization can be accomplished is a particularly advantageous feature of the present invention.

For olefin hydrogenation the pressure will range from about 100 psig to about 1000 psig with a pressure in the range of about 100 psig to about 500 psig being preferred. Again the pressure is the sum of the partial pressure of the fluid stream plus the partial pressure of the added hydrogen.

The pressure of the fluid stream being treated is not believed to have an important effect on the absorption process of the present invention. The pressure will be in the range of from about atmospheric to at least 2,000 psig during the treatment.

Any suitable quantity of hydrogen can be added to accomplish the hydrodesulfurization and/or olefin hydrogenation. The quantity of hydrogen used to contact the fluid stream containing the organic sulfur compounds being hydrodesulfurized will generally be in the range of about 100 to about 10,000 SCF/bbl and will more preferably be in the range of about 250 to about 3,000 SCF/bbl. For olefin hydrogenation, the hydrogen concentration should be at least sufficient to hydrogenate all olefins, i.e., mole percent hydrogen added should equal mole percent olefins. Preferably, the mole percent hydrogen will be 2–3 times the mole percent of olefins. The presence of additional hydrogen is not required for the absorption process.

Any suitable residence time for the fluid stream in the presence of the absorbing composition of the present invention can be utilized. Where the fluid stream is a liquid, the residence time in terms of the volumes of liquid per volume of absorbing composition per hour will generally be in the range of about 0.1 to about 50 and will more preferably be in the range of about 1 to about 20. Where the fluid stream is a gaseous stream, the residence time expressed as volumes of gas at standard temperature and pressure per volume of absorbing composition per hour will generally be in the range of about 10 to about 10,000 and will more preferably be in the range of about 250 to about 2500.

The absorbing composition of the present invention continues to be effective for converting organic sulfur compounds to hydrogen sulfide or hydrogenating olefin contaminants even when completely sulfided. However, when the absorbing composition is completely sulfided it will no longer combine with the hydrogen sulfide in the manner set forth in equation (I). When this condition occurs, hydrogen sulfide will begin to appear in the effluent flowing from the reaction and this will be an indication that the absorbing composition should preferably be regenerated. The time required for the absorbing composition to become completely sulfided will generally be a function of the concentration of sulfur in the feedstock and feed rate employed.

When the absorbing composition becomes substantially completely sulfided, the absorbing composition is typically regenerated by terminating the flow of feed to the reactor and purging with an inert fluid such as nitrogen to remove any combustibles. A free oxygen-containing fluid is then introduced to oxidize the zinc sulfide in accordance with equation (II). Also at the temperature at which the oxidation of the zinc sulfide is effected, the zinc oxide thus produced recombines with the titanium dioxide to resynthesize the original zinc titanate in accordance with equation (III).

If only olefin hydrogenation is occurring, the regeneration step may be utilized to remove coke from the promoted zinc titanate when the catalyst becomes fouled. If absorption is occurring, the promoted zinc titanate will generally become completely sulfided long before the formation of coke becomes a problem. Thus, sulfiding of the catalyst generally determines the length of the reaction period if absorption is occurring.

If absorption is occurring, the amount of oxygen, from any source, supplied during the regeneration step will generally be in an amount sufficient to at least substantially remove sulfur from the absorbing composition. The regeneration step is conducted at generally about atmospheric pressure. The temperature for the regeneration step is preferably maintained in the range of about 370° to about 815° C. and is more preferably maintained at about 540° C. in order to both oxidize the zinc sulfide and convert the zinc oxide and titanium dioxide to zinc titanate within a reasonable time. If absorption is not occurring, the amount of oxygen, from any source, supplied during the regeneration step will be at least the amount sufficient to remove substantially all carbonaceous materials from the promoted zinc titanate.

Examination of absorbing composition from various stages of the cyclic process confirms the suppositions made by observing reaction products from process studies. Zinc titanate promoted with about 18 weight percent of cobalt and molybdenum oxides shows an X-ray diffraction pattern of only the $Zn_2TiO_4$. When completely sulfided, the X-ray diffraction pattern becomes zinc sulfide (both wurtzite and sphalerite) and titanium dioxide (anatase only). After regeneration with air, the absorbing composition again has an X-ray diffraction pattern identical with that of the original material except for the occasional observation of traces of zinc molybdate. Presumably, both the cobalt and molybdenum follow the zinc in being oxides or sulfides. It has been noted that repetitive operation through these cycles causes a significant increase in the surface area of the zinc titanate absorbing composition. The surface area of the zinc titanate absorbing composition is higher in the sulfided form than in the oxidized form. Reformation of zinc titanate in this process occurs at a temperature significantly lower than that required to synthesize the material when starting with the pure oxides.

The following examples are presented in further illustration of the invention.

EXAMPLE 1

Zinc titanate having an atomic ratio of Zn:Ti = 2.0:1 was prepared by mixing 162.8 g (2 moles) of Mallinckrodt zinc oxide with 79.9 g (one mole) of Cab-O-Ti titanium dioxide (flame hydrolyzed) in 1200 mL of water in a blender for 10 minutes. The resulting slurry was oven dried at 105° C. and then calcined in air for 3 hours at 816° C. After cooling, the thus calcined material was crushed and screened. Portions of the screened zinc titanate having the size set forth in Table I were modified by the addition of various promoters to produce absorbing compositions A-G.

The general method for preparing each absorbing composition was as follows. A weighed portion of zinc titanate, prepared as previously described, having a known pore volume was covered with a solution (generally aqueous) of known concentration of the promoting element. After standing one hour at 25° C., excess solution was removed by decanting or filtering and the wet catalyst was dried, with occasional stirring, in an oven, on a hot plate, or under a heat lamp. The dried catalyst was calcined in air in a muffle furnace for 3–4 hours at 538° C., cooled in a desiccator, and reweighed. The quantity of promoter added by this procedure was considered to be calculable from the volume of promoter solution contained in the pores of the zinc titanate. Occasionally, this quantity was checked by observing the gain in weight of the absorbing composition made as described, but this gain was not considered to provide a definitive value of concentration. To add more than one promoter, the entire procedure described here was repeated for each impregnation.

The concentration of the promoter in the solution used to impregnate the zinc titanate to a desired level was calculated from the formula $$\text{Promoter compound} = \frac{\text{Formula wt.}}{(\text{at. wt.}) \times n} \times \frac{\text{Vol. Solution}}{\text{pore volume}} \times \frac{\text{desired conc. of promoter, \%}}{100}$$

where n = number of atoms of promoter element per molecule of compound. To illustrate, to prepare an absorbing composition containing 8.0 weight percent molybdenum on zinc titanate that has 0.8 mL/g pore volume, using ammonium heptamolybdate tetrahydrate as the source of molybdenum.

$$\frac{1235.95}{7 \times 95.94} \times \frac{100}{0.80} \times \frac{8.0}{100} =$$

18.40 g $(NH_4)_6Mo_7O_{24} \cdot 4H_2O/100$ mL solution.

The composition, size, and surface area of absorbing compositions A–G are summarized in Table I. In every case zinc titanate comprised the unreported portion of the absorbing composition.

TABLE I

| Absorbing Compositions | Promoters, Wt. % | Size, U.S. Sieve | Surface Area m²/g |
|---|---|---|---|
| A | 6.4 CoO, 11.3 MoO₃, 0.1 Pt | −8 + 14 | 3.0 |
| B | 0.2 CoO, 0.65 MoO₃ | −16 + 40 | 5.8 |
| C | 2.8 CoO, 5.0 MoO₃ | −16 + 40 | 5.9 |
| D | 4.0 NiO, 13.0 MoO₃ | −16 + 40 | 4.3 |
| E | 7.6 NiO, 24 WO₃ | −16 + 40 | 5.8 |
| F | 2.6 Re₂O₇ | −16 + 40 | 6.0 |
| G | 13.0 MoO₃ | −16 + 40 | 5.1 |

The promoters were added as aqueous solutions of the following salts. Cobalt as $Co(NO_3)_2 \cdot 6H_2O$, molybdenum as $(NH_4)_6Mo_7O_{24} \cdot 4H_2O$, platinum as $H_2PtCl_6 \cdot 6H_2O$, nickel as $Ni(NO_3)_2 \cdot 6H_2O$, tungsten as $(NH_4)_2W_4O_{13} \cdot 8H_2O$, and rhenium as $NH_4ReO_4$.

Absorbing composition A from Table I was used in a cyclic manner for hydrodesulfurization (HDS). A complete process cycle consisted of (1) Hydrotreating 2.75 weight percent thiophene in cyclohexane (1.0 wt. % organic sulfur) at 160 psig pressure for 120 minutes between 370°–427° C. using 3.0 LHSV and adding about 0.5 mole hydrogen per mole of liquid feed, (2) Terminating the flow of the feed, (3) Purging with nitrogen for 30 minutes while temperature is increased to about 566° C., (4) Regenerating the thus purged absorbing composition A with air for 120 minutes at 566° C., (5) Terminating the flow of the air, (6) Purging with nitrogen for 30 minutes while temperature cools to about 370° C., (7) Purging with hydrogen for 30 minutes at 370°–427° C. and then introducing feed per step (1). Steps 3, 4, 6 and 7 were all made at pressures between 0–30 psig.

Results obtained through 95 cycles of operation are summarized in Table II.

TABLE II

| Cycle No. | HDS Temp., °C. | HDS wt. % of sulfur originally present | Cyclohexane Loss, % |
|---|---|---|---|
| 10 | 432 | 99 | 3 |
| 27 | 381 | 84 | 0 |
| 72 | 377 | 94 | 0 |
| 87 | 387 | 82 | 0 |
| 83–95 comp. | 388 | >90 | 0 |

During each 120 minute process cycle, 10.5 weight percent of the original sulfur required to completely sulfide the absorbing composition was introduced into the reactor. (It is believed that cobalt and molybdenum, in addition to the zinc, become sulfided.) Table II shows that hydrodesulfurization activity was sustained during the 95 cycles that absorbing composition A was used.

Absorbing compositions B through G were used in hydrodesulfurization/absorption runs that demonstrate the hydrodesulfurization/absorption process. Table III, which describes the feedstock and summarizes run conditions, shows that all of these absorbing compositions were active to hydrodesulfurize organic sulfur compounds, and frequently the absorbing composition activity improved with use. Table III also shows that after use the absorbing composition contained approximately the stoichiometric concentration of sulfur. (For reference unpromoted $Zn_2TiO_4$ in which the zinc has been completely sulfided contains 23.34 weight percent sulfur.) After regeneration the concentration of sulfur was substantially reduced. X-ray diffraction analysis indicates that the sulfur was retained in the sulfide form, not as sulfate. X-ray diffraction showed also that the predominant crystalline components of used absorbing compositions were zinc sulfide and titanium dioxide. After regeneration, zinc titanate was the principal crystalline component. Table III also shows the surface area of the sulfided catalyst to be substantially larger than that of the regenerated form of the absorbing compositions.

TABLE III

| Absorbing Compositions | No. of Regen. | HDS wt % of sulfur originally present[1] | Absorbing Composition After HDS | | | | Absorbing Composition After Regen[3] | | |
|---|---|---|---|---|---|---|---|---|---|
| | | | Wt. % S | Wt. % C | SA, m²/g | XRD[2] | Wt. % S | SA, m²/g | XRD[2] |
| B | Fresh | 85.3 | 20.3 | 0.56 | 22.5 | ZnS,TiO₂, | 0.80 | 5.3 | ZT,trZnO, |
| | 1 | 84.0 | 22.4 | 0.60 | 19.5 | trZT | ND | ND | trZnS |
| | 2 | 88.0 | 23.6 | 0.82 | ND | | 1.0 | 5.6 | |
| C | Fresh | 92.5 | 21.8 | 0.46 | 13.3 | ZnS,TiO₂, | 1.28 | 6.6 | ZT |
| | 1 | 98.9 | 27.8 | 0.83 | 21.1 | trZT | 2.0 | 8.5 | |
| | 2 | 98.9 | 20.6 | 1.01 | 20.1 | | 3.1 | 5.9 | |
| D | Fresh | 93.9 | 25.1 | 0.36 | ND | ZnS,TiO₂, | 4.45 | 8.2 | ZT,ZnS,trZnO, |
| | 1 | 98.7 | 22.6 | 0.83 | 17.6 | Ni₃S₂MoS₂ | 3.93 | 7.0 | trTiO₂,trZnMoO₄ |
| E | Fresh | 94.7 | 15.2 | 0.39 | ND | ZnS,TiO₂ | 8.34 | ND | ZT,ZnS,ZnO |

TABLE III-continued

| Absorbing Compositions | No. of Regen. | HDS wt % of sulfur originally present[1] | Absorbing Composition After HDS | | | | Absorbing Composition After Regen[3] | | |
|---|---|---|---|---|---|---|---|---|---|
| | | | Wt. % S | Wt. % C | SA, m²/g | XRD[2] | Wt. % S | SA, m²/g | XRD[2] |
| F | 1 | 90.9 | 15.9 | 0.29 | 8.2 | ZT,ZnWO₄ | | 7.2 | TiO₂,ZnWO₄ |
| | Fresh | 80.5 | 20.8 | 0.36 | 14.9 | ZnS,TiO₂ | 4.86 | 9.6 | ZT,trTiO₂, |
| G | 1 | 92.3 | 22.0 | 0.55 | 25.0 | | ND | ND | |
| | Fresh | 87.5 | 22.6 | 0.47 | ND | ZnS,TiO₂ | 1.37 | ND | ZT,ZnMoO₄ |

[1]Tested at 399° C., 500 psig, 1.0 LHSV using feedstock from 70% straight run distillate plus 30% 105–388° C. light cycle oil (0.75 wt. % organic S in blend); 9.5 moles hydrogen per mole liquid feed; runs 24–60 hr. duration.
[2]ZnS: wurtzite plus sphalerite; TiO₂: anatase only; ZT: zinc titanate; tr: trace
[3]Absorbing composition was regenerated for 2 hours at 538° C. in air in a muffle furnace.

EXAMPLE 2

Direct comparisons of hydrodesulfurization activity were made between zinc oxide and zinc titanate where both were unpromoted, where both were promoted with molybdenum oxide only, and where both were promoted with cobalt molybdate. All runs were made over a range of temperatures at 1.0 LHSV, 500 psig reactor pressure with 5000 SCF hydrogen per barrel of feed. The feedstock was a 104°–388° C. boiling range distillate that contained 0.73 wt. % organic sulfur. Girdler G-720 zinc oxide (a commercial desulfurization catalyst) and zinc titanate synthesized as described in Example 1 were used to make these runs. Promoters were added to the zinc oxide and zinc titanate using the method described in Example 1. In all cases the absorbing composition were −20+40 mesh U.S. sieve fraction. All catalysts were regenerated in air for two hours at 538° C.

Results from runs with unpromoted zinc oxide and zinc titanate are summarized in Table IV.

TABLE IV

| | ZnO | | Zn₂TiO₄ | |
|---|---|---|---|---|
| | Fresh | Regen. | Fresh | Regen. |
| Absorbing Composition Surface area, m²/g | 10.5 | 10.5 | 7.6 | 7.6 |
| HDS, wt % of sulfur originally present: | | | | |
| 650° F. | 40.0 | 22.7 | 28.0 | 33.3 |
| 700 | 49.3 | 29.3 | 46.7 | 43.3 |
| 750 | 45.3 | 42.7 | 54.7 | 60.0 |
| 775 | 53.3 | 52.0 | 66.7 | 70.7 |
| Absorbing Composition Inspection: | | | | |
| Carbon, wt. % | 0.34 | 0.28 | 0.30 | 0.57 |
| Sulfur, wt. % | | | | |
| After HDS | 15.0 | 18.8 | 13.3 | 17.6 |
| After regen. | 11.9 | 11.7 | 7.1 | 10.8 |
| XRD analysis after HDS: | ZnO | | Zn₂TiO₄ | |
| | ZnS | | ZnS | |
| | | | TiO₂ (anatase) | |
| XRD analysis after regen. | ZnO | | Zn₂TiO₄ | |
| | ZnS | | ZnS | |
| | ZnSO₄ | | TiO₂ (anatase) | |

Although both absorbing compositions showed significant hydrodesulfurization activity when fresh, zinc oxide was inferior at all temperatures after regeneration. In contrast zinc titanate tended to improve after regeneration. Neither absorbing composition regenerated well as indicated by their sulfur content.

Results from runs using zinc oxide and zinc titanate promoted only with molybdenum trioxide are summarized in Table V.

TABLE V

| | 12.75 wt % MoO₃/ZnO | | 13.2 wt % MoO₃/Zn₂TiO₄ | |
|---|---|---|---|---|
| | Fresh | Regen. | Fresh | Regen. |
| Absorbing Composition Surface area, m²/g | 6.5 | N.D. | 5.3 | 7.6 |
| HDS, wt % of sulfur originally present: | | | | |
| 650° F. | 75.3 | 34.7 | 63.9 | 54.7 |
| 700 | 88.1 | 48.0 | 84.7 | 81.3 |
| 750 | 95.9 | 65.3 | 97.6 | 96.0 |
| 775 | 98.1 | 72.0 | 96.1 | 97.1 |
| Absorbing Composition Inspection: | | | | |
| Carbon, wt. % | 0.35 | 0.27 | 0.72 | 0.55 |
| Sulfur, wt. % | | | | |
| After HDS | 12.0 | 28.5 | 20.3 | 21.3 |
| After regen. | 10.8 | 16.5 | 0.73 | not regen. |
| XRD analysis after HDS: | ZnS | | ZnS TiO₂ (trace rutile) | |
| XRD analysis after regen. | ZnS | | Zn₂TiO₄ ZnO-trace ZnMoO₄-trace | |

Unused zinc oxide promoted with molybdenum trioxide is seen to be excellent for hydrodesulfurization. After regeneration its hydrodesulfurization activity has decreased markedly. In contrast, zinc titanate promoted with molybdenum oxide, while possibly less active when unused, is seen to be appreciably more active after regeneration. Sulfur analyses showed that the promoted zinc titanate gave up a much larger fraction of its sulfur than the promoted zinc oxide did when regenerated. In addition the promoted zinc oxide contained enough inactive zinc sulfate (ZnSO₄) to be seen by X-ray diffraction analysis.

Results from runs using zinc oxide and zinc titanate promoted with cobalt molybdate are summarized in Table VI.

TABLE VI

| | 4.0 wt % CoO— 12.3 wt % MoO₃/ZnO | | 3.4 wt % CoO— 14.7 wt % MoO₃/Zn₂TiO₄ | |
|---|---|---|---|---|
| | Fresh | Regen. | Fresh | Regen. |
| Absorbing Composition Surface area, m²/g | N.D.** | N.D. | 8.6 | N.D |
| HDS, wt % of sulfur originally present: | | | | |

TABLE VI-continued

|  | 4.0 wt % CoO—12.3 wt % MoO$_3$/ZnO | | 3.4 wt % CoO—14.7 wt % MoO$_3$/Zn$_2$TiO$_4$ | |
| --- | --- | --- | --- | --- |
|  | Fresh | Regen. | Fresh | Regen. |
| 650° F. | 73.3 | 78.7 | 93.3 | 88.0 |
| 700 | 85.3 | 86.7 | 98.7 | 94.7 |
| 750 | 94.7 | 92.0 | 94.7 | 98.7 |
| 775 | 97.2 | 94.7 | 99.6 | 99.2* |
| Absorbing Composition Inspection: |  |  |  |  |
| Carbon, wt % | 0.30 | 0.30 | 0.65 | 0.58 |
| Sulfur, wt % |  |  |  |  |
| After HDS | 16.8 | 29.0 | 24.8 | 24.2 |
| After regen. | 13.3 | 21.2 | 1.1 | not regen. |
| XRD analysis after HDS: | ZnS ZnMoO$_4$-trace |  | ZnS TiO$_2$ (anatase) |  |
| XRD analysis after regen.: | ZnS ZnO ZnMoO$_4$ ZnSO$_4$ |  | ZnTiO$_4$ ZnO-trace ZnMoO$_4$-trace |  |

*At 800° F.; not measured at 775° F.
**Not determined but prepared by adding cobalt to the MoO$_3$/ZnO preparation of Table V; S.A.=6.5 m$^2$/g before this impregnation. Zinc oxide and zinc titanate are both effective hydrodesulfurization absorbing compositions when promoted with cobalt molybdate. However, the promoted zinc titanate was shown to be superior when fresh and also after regeneration when compared with the promoted zinc oxide. Again, the sulfur analyses showed that zinc titanate gave up a much larger fraction of sulfur than the zinc oxide did upon being regenerated.

EXAMPLE 3

Zinc titanate having an atomic ratio of Zn:Ti=1.8:1 was prepared by mixing 73.2 g (0.9 moles) of Mallinckrodt zinc oxide with 40.0 g (0.5 moles) of Cab-O-Ti titanium dioxide (flame hydrolyzed) in 600 cc of water in a blender for 10 minutes. The resulting slurry was oven dried at 105° C. and then calcined in air for 4 hours at 815° C. After cooling, the thus calcined material was crushed and screened. A −10+40 mesh fraction of the screened zinc titanate was retained to prepare absorbing compositions H and I.

Absorbing composition H was prepared by soaking 32.2 g of the zinc titanate in an excess of solution prepared by dissolving 17.42 g of (NH$_4$)$_6$Mo$_7$O$_{24}$.4H$_2$O and 19.02 g of Co(NO$_3$)$_2$.6H$_2$O in water containing sufficient ammonia to completely dissolve the cobalt compound and diluting to 150 mL. Excess solution was removed by filtration. The resulting residue was dried and calcined in air at 538° C. for one hour. The resulting solid (absorbing composition H) contained, by chemical analysis, 2.80 weight percent CoO and 7.95 weight percent MoO$_3$, and had a surface area of 5.9 m$^2$/g.

Absorbing composition I was prepared by soaking 55 g of the zinc titanate in an excess of solution containing 17.4 g of (NH$_4$)$_6$Mo$_7$O$_{24}$.4H$_2$O/100 mL. Excess solution was removed by filtration. The resulting residue was dried and calcined in air at 538° C. for one hour. After cooling the resulting solid was soaked in a solution that contained 20.9 g of Co(NO$_3$)$_2$.6H$_2$O/100 mL. Again excess solution was removed by filtration. The resulting residue was dried and calcined in air at 538° C. for one hour. The resulting solid absorbing composition I contained, by chemical analysis, 5.21 weight percent CoO and 13.35 weight percent MoO$_3$, and had a surface area of 6.5 m$^2$/g.

Prior to being used as a hydrogen sulfide absorbent, absorbing composition H was used as a catalyst to hydrodesulfurize a petroleum fraction. Absorbing composition H was subjected to three periods of sulfiding followed by oxidative regeneration. Hydrodesulfurization runs were at 500 psig using temperatures between 315°–427° C.--conditions equivalent to those desired for H$_2$S adsorption. Regeneration was with air for two hours at 538° C. The absorption process is illustrated by the sulfur content of absorbing composition H determined by chemical analysis of a small, representative sample from each phase of the operation as is set forth in Table VII.

TABLE VII

| Original sample | 0.00 wt. % sulfur |
| --- | --- |
| After 1st HDS run | 21.8 wt. % sulfur |
| After 1st regeneration | 1.28 wt. % sulfur |
| After 2nd HDS run | 27.8 wt. % sulfur |
| After 2nd regeneration | 3.87 wt. % sulfur |
| After 3rd HDS run | 20.6 wt. % sulfur |
| After 3rd regeneration | 3.09 wt. % sulfur |

Elemental analysis, weight changes, and X-ray diffraction data of absorbing composition H after each hydrodesulfurization period and each regeneration period showed no evidence of formation of inactive ZnSO$_4$.

Following the three hydrodesulfurization periods and the three regeneration periods set forth in Table VII, absorbing composition H supplemented with 3.75 g of fresh absorbing composition H to replace the portion of absorbing composition H which had been expended for chemical analyses to obtain the data set forth in Table VII, was used in a run to remove hydrogen sulfide from a gas mixture prepared to simulate natural gas. The gas mixture was a blend synthesized to contain nominally five mole percent each of hydrogen sulfide and carbon dioxide in methane. The gas mixture was passed through a stainless steel tube reactor mounted vertically in an electrically heated tube furnace at a space rate of 366 hr.$^{-1}$ for 4.5 hours at 373° C. and atmospheric pressure. The stainless steel tube contained absorbing composition H. Analyses of effluent gas made during the run using Drager tubes (calibrated colorimetric detectors from National Drager, Inc., Pittsburgh, PA, and available through laboratory and safety equipment suppliers) were consistently negative, indicating that less than 0.04 ppm hydrogen sulfide remained in the gas. Analyses in triplicate of the feed sample and the effluent product by gas-liquid chromatography (GLC) for carbon dioxide showed 6.49 and 6.74 mole percent, respectively. These concentrations show that essentially none of the carbon dioxide was removed from the methane while no detectable amount of hydrogen sulfide was found in the effluent. At the conclusion of the run about 41 percent of the zinc in absorbing composition H had been sulfided.

Prior to being utilized as a hydrogen sulfide absorbent, absorbing composition I was used as a catalyst to hydrodesulfurize a petroleum fraction. Absorbing composition I was subjected to two periods of hydrodesulfurization with a regeneration period between the two hydrodesulfurization periods. Hydrodesulfurization runs were at 500 psig using temperatures between 315° and 427° C. Regeneration was with air for two hours at 538° C. The absorption process is illustrated by the sulfur content of absorbing composition I determind by chemical analysis of a small, representative sample from each phase of the operation as set forth in Table VIII.

TABLE VIII

| Original sample | 0.00 wt. % sulfur |
|---|---|
| After 1st HDS run | 21.0 wt. % sulfur |
| After 1st regeneration | 8.0 wt. % sulfur |
| After 2nd HDS run | 23.2 wt. % sulfur |

24.26 g of absorbing composition I remained after the analysis was performed after the second hydrodesulfurization run set forth in Table VIII. The remaining portion of absorbing composition I was regenerated in air at 538° C. for two hours and then used, without being analyzed for sulfur, in a run to remove hydrogen sulfide from the effluent of an operating hydrodesulfurization process. The hydrodesulfurization effluent contained, by analysis, 0.49 mole percent hydrogen sulfide. The concentration of the other components of the hydrodesulfurization effluent was not determined although the hydrodesulfurization effluent was known to be principally hydrogen with small amounts of hydrocarbons. Absorbing composition I was contained in a stainless steel tube reactor which was mounted vertically in a tube furnace. The hydrodesulfurization effluent was passed over absorbing composition I at a space rate of 1200 hours$^{-1}$ for 5.5 hours at a temperature of 400° C. and atmospheric pressure. Analysis of the hydrodesulfurization effluent, after the hydrodesulfurization effluent had been contacted with absorbing composition I, with Drager tubes was negative which indicates that the hydrogen sulfide concentration was less than 0.04 ppm.

The temperature of absorbing composition I was reduced to 204° C. and the hydrodesulfurization effluent was passed over absorbing composition I in the stainless steel reactor at a space rate of 1200 hour$^{-1}$, for 4 hours at atmospheric pressure. At the lower temperature of 204° C., about 5 ppm hydrogen sulfide remained in the hydrodesulfurization effluent after the hydrodesulfurization effluent had been contacted with absorbing composition I.

EXAMPLE 4

A catalyst having a composition nearly identical to that of absorbing composition H, in Example 3, was used to purify isobutane that was to be used as an aerosol propellant. The catalyst contained 2.6 wt. % CoO, 8.3 wt. % MoO$_3$, had 9.8 m$^2$/g surface area and 1.12 g/mL bulk density. Thirty mL of −20+40 mesh catalyst, loaded into a tubular reactor, was placed in a vertical, electrically heated, temperature controlled furnace. Isobutane at 17.5 LHSV plus hydrogen at 215 SCF/bbl passed downflow through the reactor at 300° C. and 1.34 MPa. The isobutane initially contained 2 parts per million total sulfur and from 20 to 150 parts per million olefins. After treatment as described, it contained less than five parts per million olefins as measured by GLC, and had no sulfur or unpleasant odor.

Reasonable variations and modifications are possible within the scope of the disclosure and the appended claims to the invention.

That which is claimed is:

1. A process for hydrogenating olefin contaminants contained in a fluid stream comprising the step of contacting said fluid stream under suitable hydrogenation conditions with a catalyst composition comprising zinc titanate and at least one promoter selected from the group consisting of vanadium, chromium, manganese, iron, cobalt, nickel, molybdenum, rhenium, and compounds thereof, wherein the concentration by weight of said at least one promoter in said catalyst composition is less than the total concentration by weight of said zinc titanate in said catalyst composition.

2. A process in accordance with claim 1 wherein said fluid stream is an aerosol propellant selected from the group consisting of isobutane, n-butane, propane and mixtures of any two or more thereof and said olfin contaminant is selected from the group consisting of ethylene, propylene, n-butenes, isobutene, n-pentenes and branched pentenes.

3. A process in accordance with claim 1 wherein said zinc titanate is prepared by calcining a mixture of zinc oxide and titanium dioxide in the presence of molecular oxygen at a temperature in the range of about 650° C. to about 1050° C.

4. A process in accordance with claim 3 wherein the atomic ratio of zinc to titanium in said catalyst composition is in the range of about 1:1 to about 3:1.

5. A process in accordance with claim 3 wherein the atomic ratio of zinc to titanium in said catalyst composition is in the range of about 1.8:1 to about 2.2:1.

6. A process in accordance with claim 3 wherein said catalyst composition has been calcined in the presence of molecular oxygen at a temperature in the range of about 500° C. to about 650° C. after said at least one promoter has been added to said zinc titanate.

7. A process in accordance with claim 6 wherein the concentration of vanadium, chromium, manganese, iron, cobalt, nickel, or molybdenum as individual promoters, if present, expressed as an element, is in the range of about 0.4 to about 16 weight percent based on the weight of said catalyst composition and the concentration of rhenium as an individual promoter, if present, expressed as an element, is in the range of about 0.05 to about 2.5 weight percent based on the weight of said catalyst composition.

8. A process in accordance with claim 7 wherein the total concentration of any combination of the group from which said at least one promoter is selected, expressed as an element, is in the range of about 1 to about 28 weight percent based on the weight of said catalyst composition.

9. A process in accordance with claim 1 wherein said at least one promoter is a combination of cobalt and molybdenum.

10. A process in accordance with claim 9 wherein the cobalt:molybdenum atomic ratio in said catalyst composition is in the range of about 0.3:1 to about 0.8:1.

11. A process in accordance with claim 1 wherein said catalyst composition additionally comprises at least one oxidation promoter selected from the group consisting of ruthenium, rhodium, palladium, silver, tungsten, iridium, platinum, and compounds thereof.

12. A process in accordance with claim 1 wherein the concentration of ruthenium, rhodium, palladium, silver, iridium or platinum as individual oxidation promoters, expressed as an element, if present, is in the range of about 0.05 to about 2.5 weight percent based on the weight of said catalyst composition and the concentration of tungsten as an individual promoter, expressed as an element, if present, is in the range of about 0.4 to about 16 weight percent based on the weight of said catalyst composition.

13. A process in accordance with claim 12 wherein the total concentration of any combination of said at least one promoter and said at least one oxidation promoter, expressed as an element, is in the range of about 1 to about 28 weightpercent based on the weight of said catalyst composition.

14. A process in accordance with claim 1 wherein said suitable hydrogenation conditions comprise a temperature in the range of about 149° C. to about 538° C., a total system pressure in the range of about 100 psig to about 1000 psig, a hydrogen concentration sufficient to hydrogenate all of said olefin contaminants and a residence time for said fluid stream in the presence of said catalyst composition in the range of about 0.1 to about 50 liquid volumes of said fluid stream per volume of said catalyst composition per hour.

15. A process in accordance with claim 1 wherein said suitable hydrogenation conditions comprise a temperature in the range of about 204° C. to about 399° C., a total system pressure in the range of about 100 psig to about 500 psig, a mole percent hydrogen concentration in the range of about 2 to about 3 times the mole percent of said olefin contaminants in said fluid stream and a residence time for said fluid stream in the presence of said catalyst composition in the range of about 1 to about 20 liquid volumes of said fluid stream per volume of said catalyst composition per hour.

* * * * *